United States Patent [19]

Hayhurst

[11] Patent Number: 4,741,330
[45] Date of Patent: May 3, 1988

[54] METHOD AND APPARATUS FOR ANCHORING AND MANIPULATING CARTILAGE

[76] Inventor: John O. Hayhurst, 14751 SE. Wanda Dr., Milwaukie, Oreg. 97222

[21] Appl. No.: 848,341

[22] Filed: Apr. 4, 1986

Related U.S. Application Data

[63] Continuation of Ser. No. 496,116, May 19, 1983, abandoned, which is a continuation-in-part of Ser. No. 380,043, May 20, 1982, abandoned.

[51] Int. Cl.⁴ ............................................. A61F 5/04
[52] U.S. Cl. ............................ 128/92 YF; 128/330; 128/326; 128/335.5; 128/335; 128/337; 128/92 YD; 128/92 YC
[58] Field of Search .............. 128/130, 337, 330, 326, 128/335, 335.5, 92 YF, 92 YD, 92 YC

[56] References Cited

U.S. PATENT DOCUMENTS

| | | | |
|---|---|---|---|
| 3,123,077 | 3/1964 | Alcamo | 128/335.5 |
| 3,500,820 | 3/1970 | Almen | 128/2 |
| 3,527,223 | 9/1970 | Shein | 128/329 |
| 3,541,591 | 11/1970 | Hoegerman | 128/335 |
| 3,699,969 | 10/1972 | Allen | 128/330 |
| 3,716,058 | 2/1973 | Tanner | 128/337 |
| 3,871,368 | 3/1975 | Johnson et al. | 128/127 |
| 3,875,648 | 4/1975 | Bone | 128/337 |
| 3,910,281 | 10/1975 | Kletschka et al. | 128/335 |
| 3,943,932 | 3/1976 | Woo | 128/303.18 |
| 4,006,747 | 2/1977 | Kronenthal et al. | 128/335 |
| 4,243,037 | 1/1981 | Smith | 128/303 R |
| 4,291,698 | 9/1981 | Fuchs et al. | 128/335 |
| 4,326,531 | 4/1982 | Shimonaka | 128/326 |
| 4,409,974 | 10/1983 | Freedland | 128/92 B |

*Primary Examiner*—C. Fred Rosenbaum
*Assistant Examiner*—Mark F. Colosimo
*Attorney, Agent, or Firm*—Stoel Rives Boley Jones & Grey

[57] ABSTRACT

A method and apparatus for anchoring and manipulating cartilage within a joint during arthroscopic surgery by piercing the cartilage with a hollow needle, in the tip of which is lodged an elongate anchoring device having a suture attached thereto. The free end of the suture passes through the bore of a hollow tube, positioned within the hollow needle behind the anchoring device, and the tube is used to push the anchoring device out of the needle tip behind the cartilage to be anchored, the anchoring device lodging in or beyond the cartilage at a non-parallel angle to the suture and thereby anchoring the suture to the cartilage. The needle and tube may be withdrawn and the cartilage manipulated by appropriate tension on the suture. In one embodiment the anchoring device may be held in the tip of the hollow needle in a deformed condition from which it resiliently resumes its usual elongate shape upon expulsion from the hollow needle. A related anchoring device for anchoring a suture to bone tissue includes barbs on its surface. A retainer is easily slidable in one direction along the suture but resists movement along the suture in the opposite direction, to hold tissue permanently in place.

7 Claims, 2 Drawing Sheets

METHOD AND APPARATUS FOR ANCHORING AND MANIPULATING CARTILAGE

This application is a continuation of application Ser. No. 496,116, filed May 19, 1983, now abandoned, which is a continuation-in-part of application Ser. No. 380,043, filed May 20, 1982, now abnadoned.

TECHNICAL FIELD

This invention relates to a device and method for holding and manipulating cartilage and similar fibrous tissue, and particularly to such a device and its use within a joint during arthroscopic surgery, and for removing such tissue from a joint once it has been surgically freed, and for permanently reattaching tissue.

BACKGROUND OF THE INVENTION

Conventional medical clamps have serious disadvantages when used for securing and manipulating cartilage within a joint during arthroscopic surgery. Primarily, such clamps do not provide adequate fixation of the tissue during surgery, the clamps having a tendency to slip off the cartilage. Additionally, the size of the clamps in relation to the relatively small space inside the joint makes it difficult to maneuver other surgical tools such as the scalpel or arthroscope within the confined space of the joint. Such clamps can also interfere substantially with the view of the inside of the joint afforded by the arthroscope. Since such clamps must be introduced into the joint through an incision, they are consequently limited in their range of manipulation by the location of the introductory incision. In order to apply a desired directional traction to the cartilage, it may be necessary to release the cartilage, reintroduce the clamps through another incision, and reclamp the cartilage. Finally, the size of the instruments involved in an arthroscopic procedure makes the use of more than one instrument through a single incision undesirable, thereby necessitating multiple incisions.

It is often desirable to attach fibrous tissue such as a ligament or tendon to a bone, or to other fibrous tissue, to promote natural healing and reattachment of such tissue after it has been torn free from its normal point of attachment. While it has been possible through an arthroscopic procedure in some instances to insert two needles and then thread both of them to form a loop of thread to reattach fibrous tissue to similar fibrous tissue, that has been a long and involved process and is therefore somewhat undesirable. The alternative of more radical arthrotomy is also undesirable because of the increased amount of trauma and resultant increased morbidity encountered in the use of such a procedure.

As is explained in the following summary and detailed description, the present invention utilizes a tool for piercing cartilage and other fibrous tissue and anchoring a suture extending therethrough, the tool including a hollow needle and a tube which is slideable therein. Some technical references that may be of general interest with respect to devices for piercing tissue and with respect to devices involving one tubular member slidable within another are as follows: Allen U.S. Pat. No. 3,699,969; Shein U.S. Pat. No. 3,527,223; Woo U.S. Pat. No. 3,943,932; Almen U.S. Pat. No. 3,500,820; Johnson et al. U.S. Pat. No. 3,871,368; and Smith U.S. Pat. No. 4,243,037. However, none of these references discloses methods or apparatus suitable for holding and manipulating cartilage during arthroscopic surgery, nor for permanently retaining fibrous tissue attached to bone structure or other fibrous tissue.

SUMMARY OF THE INVENTION

The aforementioned problems associated with use of conventional medical clamps for holding and manipulating cartilage during arthroscopic surgery are overcome by the present invention, which provides a tool and an associated method for anchoring and manipulating cartilage during arthroscopic surgery which will provide adequate fixation of the cartilage during such surgery, will minimally interfere with visibility and use of other instruments within the joint, does not require a separate incision, and provides the ability to control the anchored cartilage from a different incision without releasing such anchored cartilage or inserting multiple clamps into the joint.

An elongate, resiliently-deformable anchoring device has inclined faces at the respective longitudinal extremities thereof. A suture is attached to the anchoring device proximate the midpoint of its length. A hollow needle having an open tip and an open butt is provided in association with an open-ended hollow tube of equal or greater length than the needle, the tube being adapted to fit movably within the needle. A limiting mechanism is provided at the butt of the needle and at the corresponding portion of the hollow tube to selectively position the tube axially within the needle so that the tube does not extend into the very tip of the needle.

The anchoring device may be located within the tip of the hollow needle either in a configuration in which it is deformed into a U shape, or in its normal shape, with the suture flexed to extend parallel to one end of the anchoring device. The longitudinal extremities of the anchoring device are slanted and include respective faces which are directed inwardly toward one another when the anchoring device is deformed to a U shape within the hollow needle. The suture is attached at a location on the periphery of the device where the faces are furthest apart.

In preparation for use, the free end of the suture is passed through the bore of the needle and the tube, the tube being positioned within the needle as described above, the free end of the suture extending out of the butt of the needle and tube. The anchoring device is lodged in the tip of the hollow needle ahead of the tube by pulling on a free end of the suture extending out of the needle and tube, and either inserting an end of the anchoring device into the hollow tip of the needle, or deforming the anchoring device into a U by pulling on the free end of the suture. A removable shield is adapted to fit on the tip of the needle to prevent the sharp tip from cutting the suture or the anchoring device during the process of inserting the anchoring device into the hollow needle in the deformed configuration.

With the anchoring device located within the tip of the needle and the shield removed, if applicable, the needle assembly is inserted into a joint during a surgical procedure and is used to pierce the cartilage to be anchored, the needle passing substantially through the cartilage. In some cases it may be desirable to rotate the needle to cut an opening in the cartilage, and the needle is provided with a sharp diagonally slanted tip for that purpose. The limiting mechanism associated with the tube and needle is manipulated so that the tube may be pushed forward to the tip of the needle, expelling the anchoring device from the tip of the needle behind the piece of cartilage to be anchored. As the anchoring device is expelled from the tip of the needle behind the cartilage it resiliently resumes its ordinary elongate shape and toggle-like orientation generally perpendicular to the length of the suture. The needle and tube may then be removed from the joint, leaving the suture extending through the cartilage and out of the joint, and allowing the cartilage to be secured with the use of tension on the suture.

If it is desirable to manipulate the cartilage by pushing on it, the suture may be rethreaded or left threaded in the tube and the cartilage may then be securely held between the tube and the anchoring device by applying tension on the suture. If it is desirable to control the cartilage from a different angle, or through a different incision, a hook may be used to enter the joint through the other incision, capture the suture, and draw it out of the joint through the other incision. It will be apparent that this may be done without detaching the anchoring device from the cartilage. The cartilage may be removed from the joint by tension on the suture once the cartilage has been surgically freed from the joint.

In some instances, it will be desirable to permanently attach fibrous tissue such as tendons or ligaments to bones, and a related anchoring device is provided for that purpose. Barb-like projections are provided on the exterior of such a device to anchor it in a hole drilled for the purpose in a bone to which the fibrous tissue is to be attached. A retainer including resilient suture-engaging edges and corners is slidable along the suture in one direction and grips the suture to resist sliding of the retainer in the opposite direction. The retainer thereby maintains tension in the suture to hold the ligament or tendon attached to the bone during healing to properly reattach the tissue to the bone.

The anchoring device, suture, and retainer of the present invention may be made of material which is gradually absorbable by the body, in order to avoid prolonged irritation of surrounding tissues.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figures 1, 2, 3, 4, 5, 6, 7:
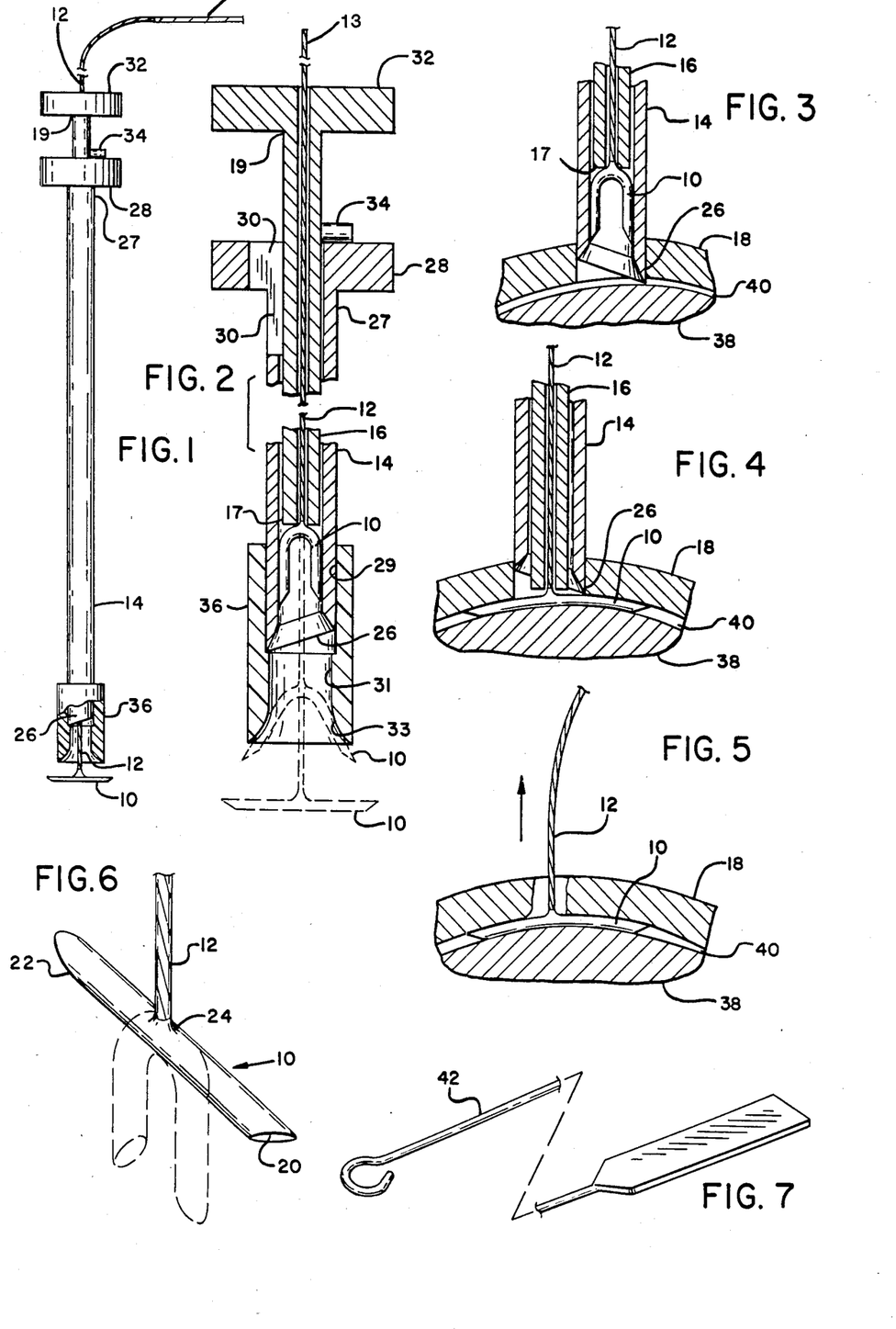
FIG. 1 is an elevational view of a cartilage anchoring tool and device according to the present invention, with a portion sectionally cut away.
FIG. 2 is a foreshortened, sectional elevational view of the cartilage anchoring tool shown in FIG. 1, illustrating the manner of deformably lodging an anchoring device within the tip of a needle thereof.
FIG. 3 is a fragmentary, sectional elevational view of the cartilage anchoring tool of FIG. 1 being used to pierce cartilage.
FIG. 4 is a fragmentary, sectional elevational view of the cartilage anchoring tool shown in FIG. 1, illustrating the manner of expelling the anchoring device behind the cartilage.
FIG. 5 is a sectional elevational view showing the cartilage secured by the anchoring device and suture shown in FIG. 1.
FIG. 6 is a perspective view of the anchoring device and suture shown in FIG. 1, at an enlarged scale, showing the deformed configuration in which the anchoring device may be lodged in the needle of the tool shown in FIG. 1.
FIG. 7 is a foreshortened perspective view of a hook for use in association with the cartilage anchoring device and suture shown in FIG. 1.

A preferred embodiment of the present invention, shown assembled in FIGS. 1 and 2, provides a resiliently deformable anchoring device IO which is attached to a suture 12 and adapted to fit deformably within the tip 26 of a hollow needle 14. A hollow tube 16, also adapted to fit within the needle 14, is used to expel the anchoring device 10 from the tip 26 of the needle once the needle has pierced a piece of fibrous tissue such as the cartilage 18 as shown in FIGS. 3 through 5, the anchoring device resiliently resuming its normal sbape behind the cartilage. The anchoring device of the invention might also be used to secure ligament or tendon tissue, as will be described hereinafter, and the term fibrous tissue will be broadly used herein to encompass cartilage, tendons, ligaments and similar tissue as differentiated from bone or soft muscle tissue.

The anchoring device 10, shown in perspective view in FIG. 6 is an elongate member, which may be cylindrical in shape and has faces 20 and 22 at the respective extremities thereof. The faces 20 and 22 preferably lie in respective planes intersecting one another in an imaginary line oriented perpendicular to the length of the anchoring device 10 and located between imaginary parallel planes perpendicular to the length of the anchoring device 10 and touching the respective ends thereof. The suture 12 is attached to the device at a location 24 on the surface of the anchoring device where the faces are furthest apart.

The anchoring device 10 is composed of a resilient material such as a plastic, which is preferably moldable and which is capable of being deformed into a U-shape as shown in broken line in FIG. 6 when drawn by the suture 12 into the needle 14 and constricted by its top 26, yet which will resiliently regain its former elongate shape when not so constricted. Although the anchoring device is shown to have a circular cross section, it is to be recognized that other cross-sectional shapes could be utilized without departing from the principles of this invention. The anchoring device 10 has a diameter, or thickness, and rigidity which are sufficient to cause it to resist deformation under slight or moderate pressure, but not so great as to prohibit the extreme U-shaped deformation within the needle as shown in FIGS. 2, 3 and 6. The material should also be sufficiently elastic to restore itself substantially to its original straight configuration shown in FIGS. 1, 4, 5 and 6. One end of the suture 12 may be securely attached to the anchoring device 10 during the molding or forming of the anchoring device. Preferably, the free opposite end 13 of the suture is hardned or stiffened as by impregnation with a suitable plastics material.

The needle 14, shown in FIGS. 1 and 2, has a hollow cylindrical shape with a sharp-edged open tip 26, an open butt 27, and a bore extending longitudinally therethrough from the tip 26 to the butt 27. The sharp tip 26 is adapted to pierce and penetrate tissue, being biased at a non-perpendicular angle with respect to the longitudinal axis of the needle and also because the cylindrical wall of the tip of the needle is beveled to create a sharp edge at the outer circumference of the needle tip 26. An annular collar 28 defining an open keyway 30 encircles the butt of the needle, the keyway extending a short distance toward the needle tip through the cylindrical wall of the needle as shown in FIG. 2.

The hollow tube 16, which is at least as long as the needle 14 and has an elongate cylindrical shape with an open tip 17 and an open butt 19, is adapted to movably fit within the hollow needle and has an interior bore diameter large enough to receive the suture 12 therethrough. The tube 16 has an annular flange 32 encircling the butt 19 thereof to prevent the tube, when pushed toward the needle tip 26, from protruding more than a predetermined distance beyond the tip, the tube preferably being of such a length that when the flange 32 is positioned immediately adjacent the collar 28 the tip 17 of the tube is proximate the needle tip 26, as shown in FIG. 4.

A limiting mechanism for providing alignment is provided in the form of a key 34, mounted on the outer cylindrical wall of the tube 16, which is adapted to mate with the keyway 30 associated with the needle 14. The key 34 will prevent the tube 16 from being introduced into the tip 26 of the needle 14 as shown in FIGS. 1 and 2 unless the key 34 is aligned with the keyway 30, alignment being accomplished by rotation of the tube 16 within the needle 14. If the tube 16 is of the aforementioned preferred length, the key 34 should be located close enough to the tip 17 to permit the anchoring device 10 to be fully drawn into the needle tip 26 when the tube is positioned inside the needle with the key and keyway out of alignment, as shown in FIGS. 2 and 3. As will be apparent, the keyway 30 should be of sufficient length to allow the flange 32 to contact the collar 28 when the key 34 is positioned in the keyway 30. It should be recognized that, while the aforedescribed key and keyway arrangement is believed to be particularly suitable, other mechanisms for limiting the protrusion of the tube 16 into the needle 14 could be utilized without departing from the principles of this invention.

As shown in FIGS. 1 and 2, a shield 36 having a generally cylindrical shape with open ends is adapted to fit removably on the sharp needle tip 26. The inner walls of the shield have three distinct sections, the upper section 29 being cylindrical and having an inner diameter substantially equal to the outer diameter of the needle tip 26 so as to permit the shield to be mounted on the tip 26, the intermediate section 31 also being cylindrical and having an inner diameter slightly smaller than the outer diameter of the needle tip 26, to shield the anchoring device from the sharp edge of the needle tip, and the lower section 33 having a truncated conical or bell-like flared shape to encourage appropriate deformation of the anchoring device 10 as it is drawn into the needle tip 26 as shown in FIG. 2.

In operation, the tool preferably is first assembled as shown in FIGS. 1 and 2, the shield 36 being mounted upon the tip 26 prior to the suture 12 being threaded through the needle 14 and out the butt 27 thereof. Tension on the free end 13 of the suture 12 which protrudes from the butt of the needle will pull the anchoring device 10 into the tip 26 as shown in FIG. 2, the inner surface of the conical or bell shaped lower section 33 of the shield guiding the anchoring device into the appropriate U-shape, the anchoring device being protected form the sharp tip by the shield 36. The tube 16 is axially positioned within the needle by the key 34 abutting against the collar 28 so that there is appropriate space for the anchoring device to lodge deformably within the needle tip 26. Positioning the tube 16 within the needle as shown in FIGS. 1 and 2 is not necessary prior to introducing the free end 13 of the suture 12 into and through the bore of the needle 14, but having the tube so positioned when the anchoring device 10 is drawn into the tip 26 is helpful to ensure that the anchoring device 10 is not positioned an unnecessary distance from the tip 26. Once the anchoring device 10 is deformably lodged in the tip 26 the shield 36 may be removed.

The assembled tool may then be introduced into the joint of a patient, either through an incision or by using the needle 14 to pierce the skin and surrounding tissue. The tip 26 of the needle 14 is thereafter used to pierce the cartilage 18 which is to be anchored, as shown in FIG. 3. Typically, the needle 14 is prevented from penetrating too far into the joint by the presence of bone 38 behind the cartilage 18, and when the bone is very close to the cartilage it may be necessary to rotate the needle 14 so that the sharpened edge of the tip 26 cuts through the cartilage.

Once the tip 26 has pierced the cartilage 18, the tube may be axially rotated within the needle 14 so that the key 34 aligns with the keyway 30. The tube 16 may then be pushed further into the tip 26 of the needle 14, the key 34 entering the keyway 30, and the tip 17 of the tube 16 expelling the anchoring device 10 from the needle tip 26 as sbown in FIG. 4. As the anchoring device 10 is pushed from the needle tip 26 it resumes its normal elongate shape as nearly as the space 40 between the bone 38 and the cartilage 18 permits, the slanted faces 20 and 22 ensuring that the longitudinal extremities of the anchoring device 10 do not catch on the bone or cartilage and thereby prevent the anchoring device from resuming its elongate shape.

Once the anchoring device 10 has generally resumed its normal elongate shape behind the cartilage 18, the needle 14 and the tube 16 may be withdrawn from the joint, allowing the cartilage 18 to partially collapse around the anchoring device 10 and suture 12 as shown in FIG. 5. The suture 12 is now anchored to the cartilage 18 and the cartilage may be securely held and manipulated by tension on the suture 12 to facilitate further surgical procedures on and around the cartilage.

The relatively small size of the suture 12 allows virtually unobstructed vision of the interior of the joint through the arthroscope, and also permits the introduction of other surgical tools such as the arthroscope or scalpel through the same incision as the suture. Due to the flexibility of the suture 12, tension may be applied from many directions as dictated by the needs of the surgical process. Further control of the cartilage 18 is available by rethreading the tube 16 on the suture 12 and applying tension to the suture, thereby effectively clamping the cartilage 18 between the anchoring device 10 and the tip 17 of the tube 16, and allowing the cartilage to be pushed, rather than pulled, into a desired position.

A hook 42, shown in FIG. 7, may be used to achieve even greater maneuverability of the anchored cartilage 1B, by introducing the hook 42 into the joint through a separate incision, capturing the suture 12 in the hook within the joint and drawing the suture 12 out of the joint through such other incision, simultaneously releasing the free end of the suture. The cartilage may then be manipulated and controlled in the manner described above, through a different incision, without detaching the anchoring device 10 from the anchored cartilage 18.

Figures 8, 9, 10, 11, 12, 13:
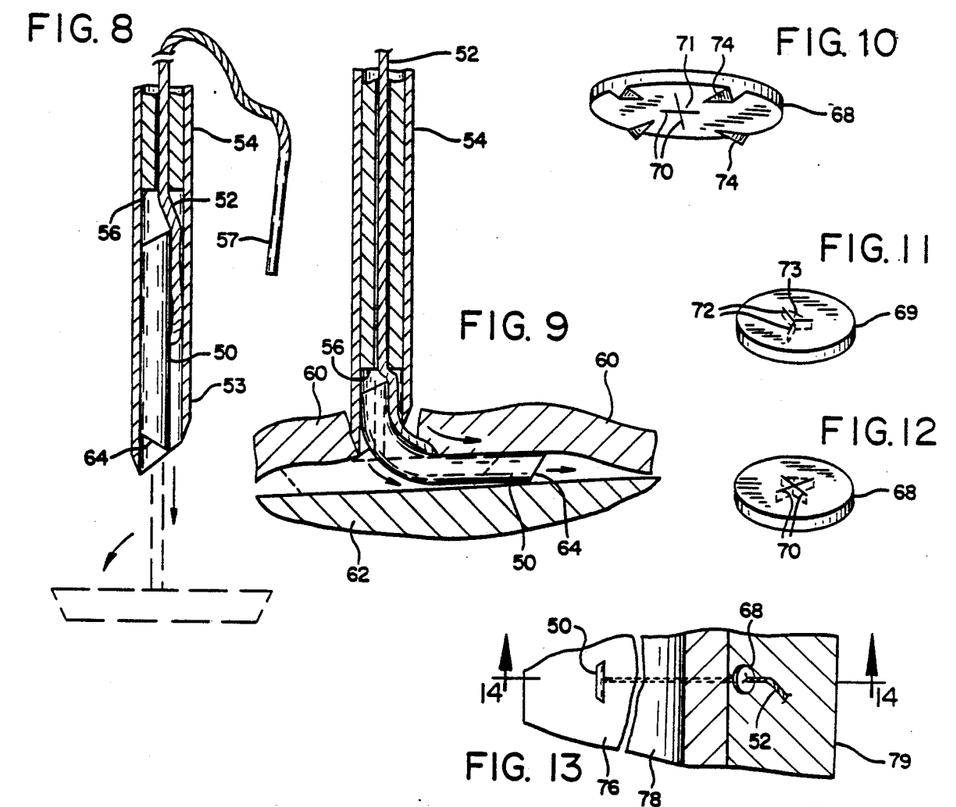
FIG. 8 is a sectional elevational view of a cartilage anchoring tool illustrating an alternative manner of lodging the anchoring device within the tip of a needle portion thereof.
FIG. 9 is a sectional elevational view of the cartilage anchoring tool shown in FIG. 8, illustrating the position of the cartilage anchoring device during expulsion from the tip of the needle.
FIG. 10 is a perspective view of the inner surface and an edge of a retainer button for use in association with the suture of the anchoring device.
FIG. 11 is a perspective view of the outer surface and an edge of another retainer device similar to that shown in FIG. 10.
FIG. 12 is a perspective view of the outer surface and an edge of a retainer such as that shown in FIG. 10.
FIG. 13 is a top view of a portion of a joint in which the anchoring device shown in FIG. 8 is being used to connect and retain a piece of cartilage in position against another piece of cartilage from which it had been torn, with the retainer of FIG. 10 being used in conjunction therewith.
Figure 14:
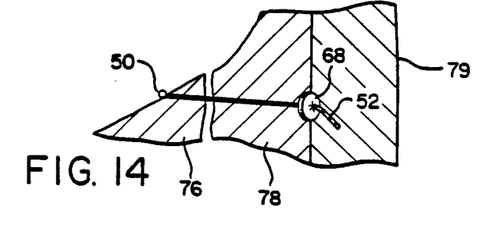
FIG. 14 is a sectional side elevational view of the joint shown in FIG. 13, in which the device of the invention is being used in conjunction with the retainer shown in FIG. 10 taken along line 14-14.

When the surgical procedure is completed, and the anchored cartilage 18 has been surgically freed, the cartilage may be removed from the joint by tension on the suture 12. Referring now to FIGS. 8 and 9, an anchoring device 50 which is similar to the anchoring device 10 described above has fixedly attached thereto a suture 52. The anchoring device 50 is held within the tip portion 53 of a hollow needle 54, ahead of the tip 56 of a hollow tube. The free end 57 of the suture 52, like the free end 13 of the suture 12, is preferably stiffened by impregnation with a plastic material or the like, and the suture 52 extends through the hollow tube 56.

As shown in FIGS. 8 and 9, the anchoring device 50 may be used in essentially the same fashion as is the anchoring device 10, with the hollow needle 54 piercing a piece of fibrous tissue such as the cartilage 60 and the anchoring device 50 thereafter being expelled from the tip of the hollow needle 54 by extension of the hollow tube 56 within the hollow needle 54. The anchor device 50 thereafter assumes a position outside the cartilage 60, between the cartilage 60 and a bone 62, where it extends generally perpendicular to the suture 52. The slanting faces 64 of the anchoring device 50 assist in directing the anchoring device 50 to this toggle-like position by their inclination to the length of the anchoring device, and for that reason it is preferable to have the suture 52 extend from the side of the anchoring device at which the length is greatest, as is shown in FIGS. 6, 8, and 9. Once the anchoring device 50 has been expelled from the needle 54, the suture 52 should be pulled outwardly to move the anchoring device 5D to the position shown in broken line in FIG. 9, where it extends laterally along the lower surface of the cartilage 60.

Referring now to FIGS. 10-14, retainer devices 68 and 69, each having a pair of generally parallel surfaces, are made of resilient material defining slits 70 or 72, respectively, which intersect near the central points of the parallel surfaces, defining pointed corner flaps 71 and 73, respectively. The retainers 68 and 69 are circular in shape for the sake of convenience. It will be understood, however, that this shape is a matter of choice and that other shapes would also be acceptable, although the circular shape may to some extent reduce the possibility of irritation of surrounding tissue. Raised points 74 are provided on the inner surface of the retainer 68 to bear against tissue and assist in immobilizing it while the anchoring device of the invention is in use.

The retainers 68 and 69 may be used in conjunction with the anchoring devices 10 and 50 by inserting the free end 13 or 53 of the suture through the retainer at the intersection of the slits 70 or 72 after the hollow needle and hollow tube have been withdrawn from around the suture. When the suture 12 or 52 is inserted through the retainer the flaps of material defined between adjacent slits are resiliently deformed toward the direction of movement of the suture therethrough. Thereafter the flaps wedge against the suture and resist withdrawal of the suture. By applying tension on the suture 52 (see FIGS. 13 and 14) and urging the retainer 68 or 69 along the suture to the surface of tissue 76 from which the suture extends, the retainer may be used to maintain tension in the suture, thereby holding a torn piece of tissue 76 against the stable piece of tissue 78 from which the piece of tissue 76 had been torn or fractured. The anchoring device 50, suture 52, and retainer 68 or 69 may then be left permanently in the joint to retain the torn cartilage 76 in its proper location against the stable cartilage 78, with the retainer 68 resting against the outside of the stable cartilage 78, between the surface of the stable cartilage 78 and muscle tissue 79 adjacent thereto.

In an anchoring device 50 or 10 to be used in this manner to permanently connect tissue, it is particularly desirable to make the anchoring device and retainer of a material which can be gradually absorbed by the body of the patient as healing occurs, to prevent prolonged irritation of the surrounding tissue by the presence of the anchoring device and retainer. Synthetic materials which have been found to be gradually absorbable by the body, as well as being moldable, are known for use in sutures and are desirable as materials for the anchor devices and retainers of the present invention. One such material which is preferred is an absorbable polymer known as poly-diaxanone (PDS), which is available from Ethicon, Inc., of Summerville, N.J.

Figure 15:
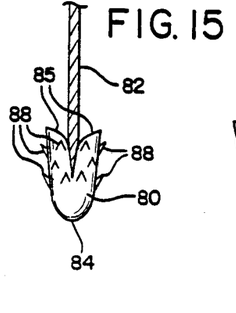
FIG. 15 is a side elevational view of an anchoring device adapted for use in anchoring a suture in bone tissue according to the present invention.
Figure 16:
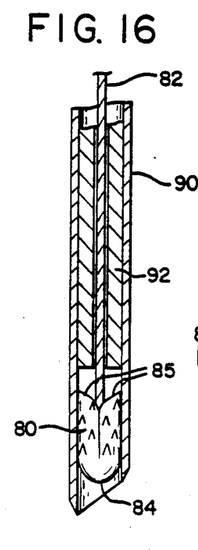
FIG. 16 is a sectional elevational view of a portion of a cartilage anchoring tool according to the present invention with the suture anchoring device shown in FIG. 15 lodged within the hollow needle thereof in readiness for use.
Figure 17:
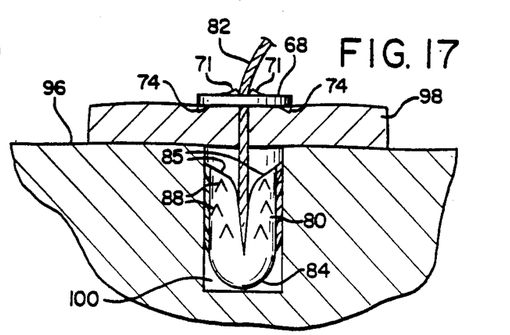
FIG. 17 is a sectional elevational view showing the anchoring device shown in FIG. 16, in use in conjunction with the anchoring retainer shown in FIG. 10, to attach a ligament to a bone.

Referring now to FIGS. 15-17, an anchoring device 80 is particularly adapted for use in anchoring sutures to bones so that the retainer 68 or 69 may be used in conjunction with a suture 82 attached to the anchoring device 80 to attach tissue to a bone. The anchoring device 80 preferably has a rounded convex front end 84 which may be formed by folding an elongate anchor body member into a U shape, with the point of attachment of the suture 82 to the anchoring device 80 being at the inside of the base of the U. Preferably each end of the elongate body has slanted end faces 85, oriented in this case, however, oppositely to the preferred orientation of the faces 20 and 22 in the anchoring device 10. When the ends of the body member are folded into a U shape alongside the suture 82 the slanting end faces 85 are inclined so as to leave a sharp edge extending toward the direction in which the suture extends away from the anchoring device 80, and defining a concave rear end of the anchoring device 80. Additionally, a plurality of barbs 88 are located on the exterior surfaces of the anchoring device 80. The barbs 88 extend outwardly, and away from the rounded convex front end 84, thus exposing a sharp edge of each barb 88 directed generally toward the direction in which the suture 82 extends away from the anchoring device 80.

As shown in FIG. 17, the anchoring device 80 is inserted for use in a manner similar to the use of the anchoring devices 10 and 50, in that it is lodged within the hollow tip of a hollow needle 90 ahead of the tip of a tube 92 which is used to expel the anchoring device 80, the suture 82 extending through the tube 92. The anchoring device 80 is particularly adapted for anchoring the suture 82 to bone 96 by insertion of the hollow needle 90 through tissue such as ligament tissue 98 and ejecting the anchoring device 80 into a socket 100 drilled in the bone 96 for the purpose of receiving the anchoring device 80. Upon expulsion from the needle 90, the retainer 68 may be used to apply tension to the suture 82 and retain the ligament 98 in position against the bone 96.

Referring again to FIGS. 8 and 3, while the tip of the needle may be beveled either to create a sharp edge at the outer circumference of the needle tip 26, as shown in FIG. 3, or at the inner circumference of the needle tip 102, as shown in FIG. 8, the latter bevelling is preferred in order to prevent a plug of material from becoming too firmly lodged inside the tip.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A device for use in anchoring and manipulating fibrous tissue such as cartilage and the like within a joint of a patient during a surgical procedure, comprising:
   (a) anchoring means, including an elongate member, for attaching a suture to fibrous tissue, said anchoring means being adapted to fit within an open tip of a hollow needle;
   (b) a suture, attached to said anchoring means medially of said elongate member thereof; and
   (c) retainer means, easily slidable along said suture toward said anchoring means but thereafter resistant to movement along said suture away from said anchoring means, for retaining tension in said suture within tissue held between said anchoring means and said retainer means, said retainer being of resilient material having a pair of opposite surfaces and defining a plurality of intersecting slits extending therethrough between said opposite faces.

2. The apparatus of claim 1, said retainer being generally disc-like, having a pair of opposite faces, said slits intersecting with one another at a central location on said opposite faces, and there defining flexible pointed corner flap means for allowing said retainer to move along said suture in one direction but resisting movement in the opposite direction thereafter.

3. A device for use in anchoring and manipulating fibrous tissue such as cartilage and the like within a joint of a patient during a surgical procedure, comprising:
   (a) anchoring means, including an elongate member, for attaching a suture to fibrous tissue, said anchoring means being adapted to fit within an open tip of a hollow needle;
   (b) a suture, attached to said anchoring means medially of said elongate member thereof; and
   (c) retainer means, easily slidable along said suture toward said anchoring means but thereafter resistant to movement along said suture away from said anchoring means, for retaining tension in said suture within tissue held between said anchoring means and said retainer means, said retainer including a face having protruding means for resisting lateral movement.

4. A device for use in anchoring and mainpulating fibrous tissue such as cartilage and the like within a joint of a patient during a surgical procedure, comprising:
   (a) anchorng means, including an elongate member, for attaching a suture to fibrous tissue, said anchoring means being adapted to fit within an open tip of a hollow needle and said elongate member having slanted end faces located at respective longitudinal extremities thereof, said faces lying in planes which intersect one another along a line substantially perpendicular to the length of said elongate member;
   (b) a suture, attached to said anchoring means medially of said elongate member thereof, said suture being attached to said elongate member at a point along the surface thereof opposite said line of intersection of said planes; and
   (c) retainer means, easily slidable along said suture toward said anchoring means but thereafter resistant to movement along said suture away from said anchoring means, for retaining tension in said suture within tissue held between said anchoring means and said retainer means.

5. A device for use in anchoring and manipulating fibrous tissue such as cartilage and the like within a joint of a patient during a surgical procedure, comprising:
   (a) anchoring means including a resiliently deformable member, for attaching a suture to bone tissue, said anchoring means being adapted to fit within an open tip of a hollow needle in a deformed configuration said anchoring means having a generally cylindrical shape, a convex nose portion, and a concave rear end;
   (b) a suture, attached to said anchoring means, said suture extending rearwardly from said rear end; and
   (c) retainer means, easily slidable along said suture toward said anchoring means but thereafter resistant to movement along said suture retaining said anchoring means, for retaining tension in said suture within tissue held between said anchoring means and said retainer means.

6. A device for use in anchoring and manipulating fibrous tissue such as cartilage and the like within a joint of a patient during a surgical procedure, comprising:
   (a) anchoring means including a resiliently deformable member for attaching a suture to bone tissue, said anchoring means being adapted to fit within an open tip of a hollow needle in a deformed configuration;
   (b) a suture, attached to said anchoring means; and (c) retainer means, easily slidable along said suture toward said anchoring means but thereafter resistant to movement along said suture retaining said anchoring means, for retaining tension in said suture within tissue held between said anchoring means and said retainer means, said anchoring means including a U shaped portion, the legs of the U extending substantially parallel with one another in the direction toward which said suture extends and being resiliently biased to separate from one another so as to bear against the interior of a socket in boe tissue when said U-shaped portion is located therein.

7. A device for securng tissue within a joint, comprising:

(a) a hollow needle havng a tip end and a butt end;

(b) an expulsion tube positionable within the hollow needle to be slidable therein;

(c) an elongated anchor member positionable within the hollow needle, the anchor member having opposing end faces, at least one end face being formed in a plane that is slanted relative to the longitudinal axis of the anchor member, the anchor member being expellable from the needle by teh expulsion tube; and (d) an elongated suture having one end attached to the anchor member, the suture extending from the interor of the expulsion tube butt end when the anchor member is positioned within the needle and when the expulsion tube is positioned within the needle, the portion of the suture near the anchor member being normally flaccid and usable for securing tissue adjacent tothe expelled anchor member.

* * * * *

UNITED STATES PATENT AND TRADEMARK OFFICE
CERTIFICATE OF CORRECTION

PATENT NO. : 4,741,330
DATED : May 3, 1988
INVENTOR(S) : John O. Hayhurst

It is certified that error appears in the above-identified patent and that said Letters Patent is hereby corrected as shown below:

Column 4, line 37, "Fig. 17" should begin a new paragraph.

Column 4, line 46, "I0" should read --10--.

Column 4, line 54, "sbape" should read --shape--.

Column 5, line 25, "hardned" should read --hardened--.

Column 6, line 32, "form" should read --from--.

Column 6, line 63, "sbown" should read --shown--.

Column 7, line 28, "1B" should read --18--.

Column 7, line 39, "Referring" should begin a new paragraph.

Column 7, line 66, "5D" should read --50--.

Column 11, line 14, "boe" should read --bone--.

UNITED STATES PATENT AND TRADEMARK OFFICE
CERTIFICATE OF CORRECTION

PATENT NO.  :  4,741,330
DATED       :  May 3, 1988
INVENTOR(S) :  John O. Hayhurst It is certified that error appears in the above-identified patent and that said Letters Patent is hereby corrected as shown below:

Column 12, line 8, "teh" should read --the--.

Column 12, line 12, "interor" should read --interior--.

Column 12, line 13, the word --hollow-- has been omitted between "the" and "needle".

Signed and Sealed this

Twenty-ninth Day of November, 1988

Attest:

DONALD J. QUIGG

Attesting Officer

Commissioner of Patents and Trademarks